United States Patent
Anciso et al.

(10) Patent No.: US 6,927,174 B2
(45) Date of Patent: Aug. 9, 2005

(54) SITE-SPECIFIC METHOD FOR LARGE AREA UNIFORM THICKNESS PLAN VIEW TRANSMISSION ELECTRON MICROSCOPY SAMPLE PREPARATION

(75) Inventors: Adolfo Anciso, Richardson, TX (US); Patrick J. Jones, Allen, TX (US); Richard B. Irwin, Richardson, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 10/639,330

(22) Filed: Aug. 12, 2003

(65) Prior Publication Data

US 2005/0037625 A1 Feb. 17, 2005

(51) Int. Cl.[7] ............................................. H01L 21/461
(52) U.S. Cl. ....................... 438/712; 438/689; 438/700; 438/691; 438/745; 438/46; 438/47; 438/734
(58) Field of Search ................................. 438/712, 689, 438/46, 745, 734, 691, 47, 700

(56) References Cited

U.S. PATENT DOCUMENTS

| | | | | | |
|---|---|---|---|---|---|
| 5,129,955 | A | * | 7/1992 | Tanaka | 134/2 |
| 5,303,594 | A | * | 4/1994 | Kurtz et al. | 73/727 |
| 5,805,421 | A | * | 9/1998 | Livengood et al. | 361/736 |
| 5,882,823 | A | * | 3/1999 | Neary | 430/5 |
| 5,942,805 | A | * | 8/1999 | Winer et al. | 257/797 |
| 6,042,736 | A | * | 3/2000 | Chung | 216/33 |
| 6,069,079 | A | * | 5/2000 | Li | 438/690 |
| 6,251,782 | B1 | * | 6/2001 | Lee et al. | 438/689 |
| 6,392,229 | B1 | * | 5/2002 | Dana et al. | 250/306 |
| 6,632,575 | B1 | * | 10/2003 | Johnson | 430/5 |
| 6,639,226 | B2 | * | 10/2003 | Morio et al. | 250/491.1 |
| 2002/0137350 | A1 | * | 9/2002 | Endoh et al. | 438/700 |

* cited by examiner

*Primary Examiner*—David Zarneke
*Assistant Examiner*—Igwe U. Anya
(74) *Attorney, Agent, or Firm*—Peter K. McLarty; W. James Brady, III; Frederick J. Telecky, Jr.

(57) ABSTRACT

A method for preparing a sample includes separating a portion of substrate from a sample, performing focused ion beam milling, and removing additional sample material using an etchant.

18 Claims, 2 Drawing Sheets

SITE-SPECIFIC METHOD FOR LARGE AREA UNIFORM THICKNESS PLAN VIEW TRANSMISSION ELECTRON MICROSCOPY SAMPLE PREPARATION

TECHNICAL FIELD OF THE INVENTION

This invention relates generally to the field of sample preparation and more specifically to a method for preparing a sample for transmission electron microscopy imaging and analysis.

BACKGROUND OF THE INVENTION

Preparing samples for plan view transmission electron microscopy generally requires the use of focused ion beam (FIB) or standard chemical etching. Standard FIB sample preparation is site specific and allows a single component of a film stack within a semiconductor device to be selected for analysis, but it suffers from sample thickness variations which limit the viewing area of the sample. Standard chemical etching is only slightly site specific, and has thickness variations that are not as severe as FIB sample preparation. With standard chemical etching, however, components from film stacks within a semiconductor device are difficult to separate, and the region surrounding the sample area is often very thin leading to mechanical support problems and a possible loss of the sample. Both standard FIB milling and standard chemical etching allow for analysis of a very limited area of the sample. Accordingly, current techniques for sample preparation for transmission electron microscopy may be unsatisfactory in many applications.

SUMMARY OF THE INVENTION

In accordance with the present invention, disadvantages and problems associated with previous techniques for sample preparation for plan view transmission electron microscopy may be reduced or eliminated. According to one embodiment, a sample preparation technique includes thinning the silicon substrate beneath the area for plan view analysis using a focused ion beam, followed by a second step of using a silicon specific etch to remove the remaining substrate below the site of interest for plan view analysis.

An advantage of an embodiment of the invention includes allowing an analysis of a site of interest ten times larger than currently provided by known methods of sample preparation. Another advantage is greater structural and mechanical support for the sample during analysis. Yet another advantage includes the ability to analyze specific film layers within a semiconductor device with greater clarity and detail.

Certain embodiments of the invention may include none, some, or all of the above advantages. One or more other advantages may be readily apparent to one skilled in the art from the figures, descriptions, and claims included herein.

BRIEF DESCRIPTION OF THE DRAWINGS

For a more complete understanding of the present invention and the advantages thereof, reference is now made to the following description taken in conjunction with the accompanying drawings.

DETAILED DESCRIPTION OF THE INVENTION

Figure 1:
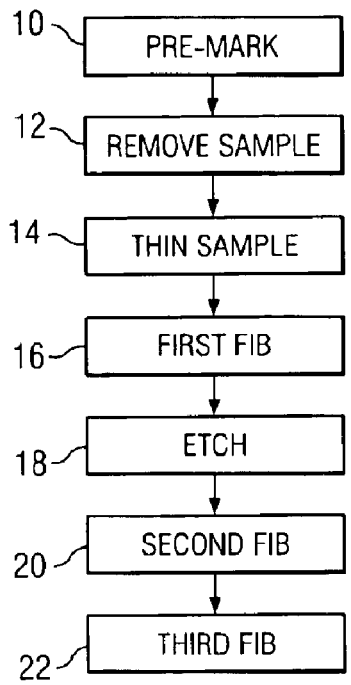
FIG. 1 is a flow chart illustrating a method according to an embodiment of the present invention.

Analysis of materials using transmission electron microscopes requires that the sample analyzed should be thin enough to allow electrons to pass through it. For silicon, electron transparency is generally achieved at a thickness of approximately 0.1 $\mu$m. Semiconductor devices often contain multiple layers of materials including, for example, one or more oxide layers disposed on or between multiple polysilicon layers, all disposed on a silicon substrate. Typical semiconductors may have a thickness of 0.1 mm to 2 mm or more. Thus, significant thinning of the semiconductor device must be performed to allow for a sample of the device to be analyzed appropriately with a transmission electron microscope.

Under current techniques, samples for analysis with transmission electron microscopes (TEMs) are prepared by either thinning the area surrounding the site of interest in the sample using focused ion beam (FIB) milling or performing an etch on the site of interest to thin the area sufficiently to allow for TEM analysis. Both FIB milling and chemical or plasma etching typically result in either a very small area that is sufficiently thin for analysis or a structurally unsound sample that is very fragile and difficult to analyze, or both. Additionally, chemical or plasma etching is often insufficiently accurate to enable analysis of a specific film within a site of interest.

According to various embodiments of the present invention, a semiconductor sample may be prepared in such a way that a larger surface area of the device may be analyzed, with increased specificity of the area to be analyzed, and increased structural stability of the sample. Standard FIB sample preparation suffers from sample thickness variations from the FIB in what is known as the classic "V" shape. Current techniques of standard FIB sample preparation result in an increased slope from the edge of the material to be analyzed, leaving an analysis region of only about 2 $\mu$m from the edge of the sample. This phenomenon occurs because of the extremely small area that can be milled and the difficulty of maintaining a consistent milling depth. The result is that when a thick layer is milled, an area of interest of the sample may be milled to the proper thickness, but areas of the sample further from the area of interest become progressively thicker, thus resulting in a cross-sectional view resembling a "V". In other words, only a limited portion of the extreme edge is thin enough for analysis.

Typical chemical etching or dimpling techniques result in concavity near the site of interest on the sample which may result in an increased dimension of analysis at the site of interest of approximately 5 $\mu$m. However, it becomes difficult to view a specific film due to the concave shape of the etch. An additional method of sample preparation known as tripod polishing also gives a uniformly increasing sample thickness similar to FIB milling, thus limiting the analysis sample size to approximately 2 $\mu$m. Additionally, this method can be quite time consuming, and components from film stacks on the semiconductor device are difficult to separate and may be polished away or may be outside the normal analysis width. Another problem with tripod polishing may include thin areas on either side of the site of interest that may reduce mechanical support rendering the sample unusable.

Referring to FIG. 1, at step 10 a site of interest is marked for easy identification on a semiconductor device using an optical microscope. Marking the site with the aid of an optical microscope may have the advantage of insuring that the sample cut from the semiconductor device or wafer is preserved throughout the sample preparation process. At step 12 the sample may be cut from the semiconductor device or wafer preferably using a dicing saw or wafer saw. In a particular embodiment the sample has a length of approximately 3 mm and a width of approximately 1 mm, wherein the site of interest is near the edge of the 3 mm side. Though the width and length of the sample is given as 3 mm and 1 mm respectively, any suitable dimensions may be used that allow for TEM analysis. Step 14 represents a first thinning step whereby the sample is thinned by removing some of the substrate from a first side with an additional cut. This first side is preferably the side which is opposite of the plan view side. In typical plan view analysis, and in accordance with an embodiment of the present invention, the term "plan view" refers to an orientation normal to the planes defined by the multiple film layers and silicon substrate of the semiconductor device.

In a particular embodiment, step 14 may reduce the thickness of the about 100 $\mu$m to 160 $\mu$m, though samples prepared according to the present invention may have thicknesses which are greater than 160 $\mu$m or less than 100 $\mu$m without exceeding the scope of the present invention. Step 14 will preferably be performed by using a wafer saw or other suitable device to mechanically separate thin layers from a semiconductor device or sample. At step 16, a second thinning step is performed so that an additional portion of the silicon substrate is cut from the sample to create a narrow strip of the silicon substrate along the edge of the sample containing the site of interest. In a particular embodiment this second thinning step 16 results in a sample having a terraced, or "step" effect wherein the thickness of the sample in the area subject to the cut of step 16 may be approximately 20 $\mu$m to 35 $\mu$m thick. Again, it should be understood that though one embodiment of the present method may result in a sample with thicknesses of 160 $\mu$m for step 14 and 35 $\mu$m after step 16, any suitable thicknesses obtained by these steps 14 and 16 may be used without exceeding the scope of the present invention. For example, the thickness after step 14 may be approximately 100 $\mu$m and the thickness after step 16 may be approximately 20 $\mu$m.

At step 18, a portion of the remaining substrate at the site of interest is removed using a focused ion beam (FIB) milling technique, wherein the remaining substrate is approximately 2 $\mu$m in a particular embodiment. At step 20, all or substantially all of the remaining substrate at the area of interest at the side opposite of the plan view side is removed using an etch. The etch of step 20 may be performed using a wet etch or a plasma etch. In a particular embodiment, the sample is etched in a solution of approximately 0.5% hydrofluoric (HF) acid for approximately three minutes to remove any native oxide. Following this initial etch, the sample is etched in chlorine for approximately one hour. It should be noted that in any particular embodiment, any silicon-specific etch may be used to remove the remaining silicon substrate on the first side of the sample at the site of interest. Examples of silicon-specific etches include chlorine, HF with nitric acid, and Tetramethyl Ammonium Hydroxide (TAMH), among others. It should also be noted that in the present embodiment the sample is still over 20 $\mu$m thick outside of the site of interest, which enhances mechanical stability. In step 22, the FIB is used to further thin the sample on the second side by removing any oxides or polysilicon layers on the plan view side of the site of interest. It should also be noted that step 22 is not required for some embodiments, depending on the particular site of interest that is to be analyzed.

Figure 2B:
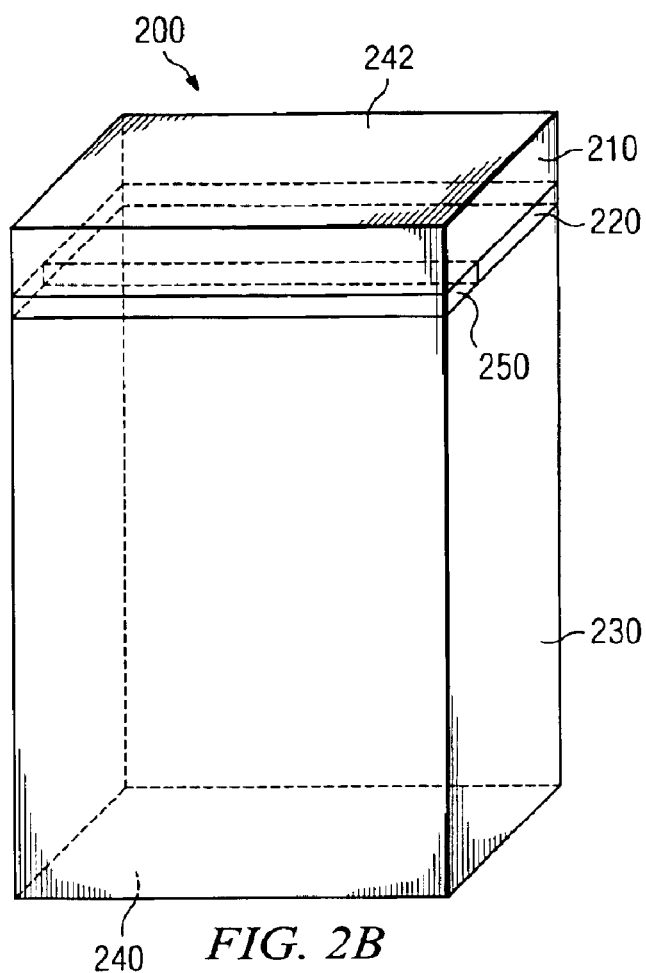
FIG. 2B is a view of a sample of the semiconductor device in FIG. 2A.
Figure 2A:
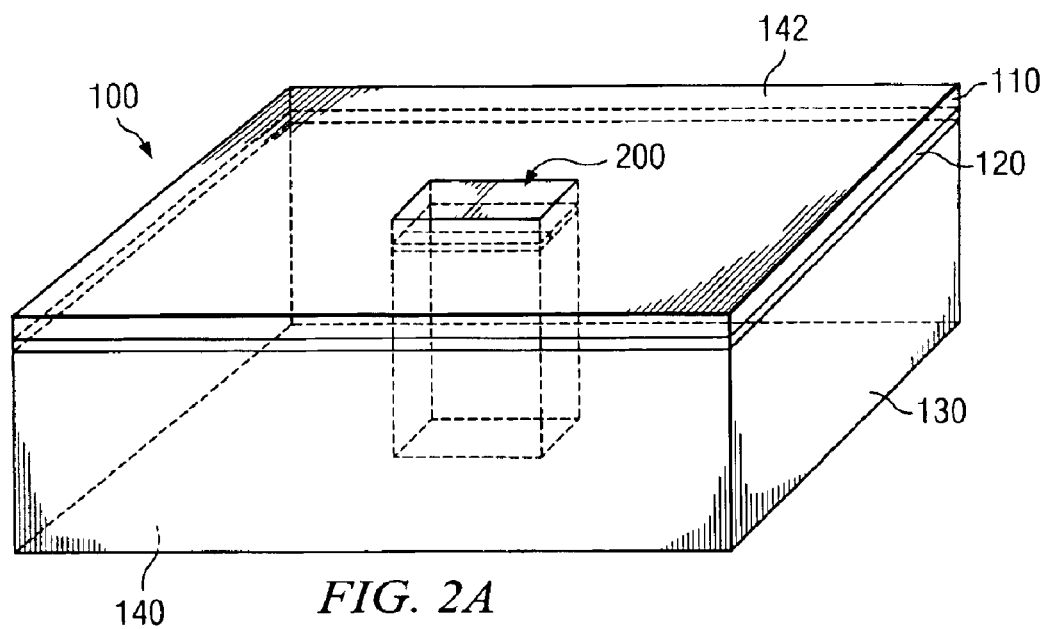
FIG. 2A is a three-dimensional view of a semiconductor device containing a site of interest therein in accordance with an embodiment of the present invention.

Referring to FIG. 2A, device 100 is a device containing a site of interest for transmission electron microscope analysis. Device 100 may have layers 110, 120 and 130, which may represent layers of oxides, polysilicon, and silicon substrate, respectively. First side 140 of device 100 is the side opposite of the plan view side of device 100 and represents a view normal to layers 110, 120 and 130 of device 100. Second side 142 represents the plan view side of device 100. Sample 200 of device 100 represents a portion of device 100 containing a site of interest for analysis by TEM. It should be noted that layers 110, 120 and 130 may contain single layers of oxides, polysilicon, and silicon substrate, multiple layers of oxides, polysilicons, and silicon substrates, or any combination of such layers and other various materials commonly known to those of ordinary skill in the art.

Referring to FIG. 2B, sample 200 has been cut from device 100 using a dicing or wafer saw, or any other method suitable for removing the sample 200 from the device 100. Sample 200, by definition, contains the same characteristics of device 100 including layers 210, 220 and 230, which correspond to layers 110, 120 and 130 of device 100. Additionally, first side 240 of sample 200 is the side opposite of the plan view side of sample 200, and second side 242 is the plan view side of sample 200. Additionally, sample 200 contains site of interest 250 which may be located in any layer 210, 220 or 230 or sample 200.

Figure 3A:
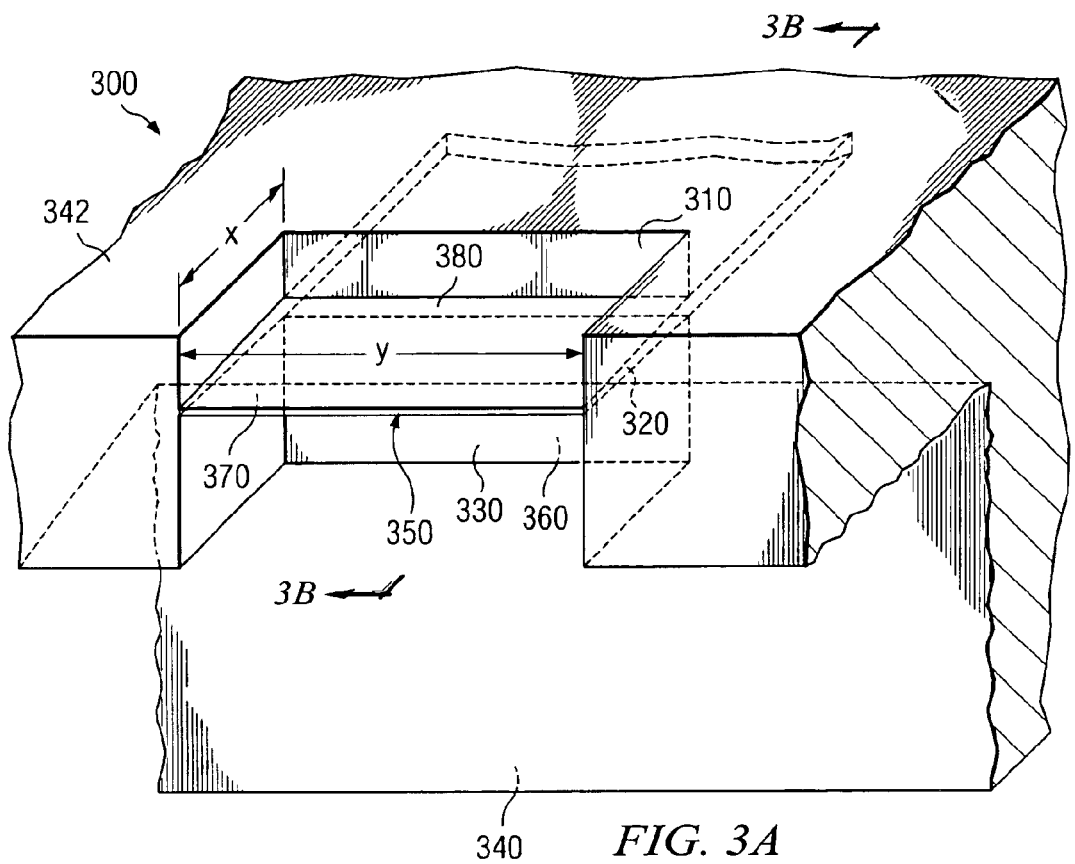
FIGS. 3A and 3B are three-dimensional and cross-sectional views of plan view of a transmission electron microscopy sample prepared in accordance with an embodiment of the present invention.
Figure 3B:
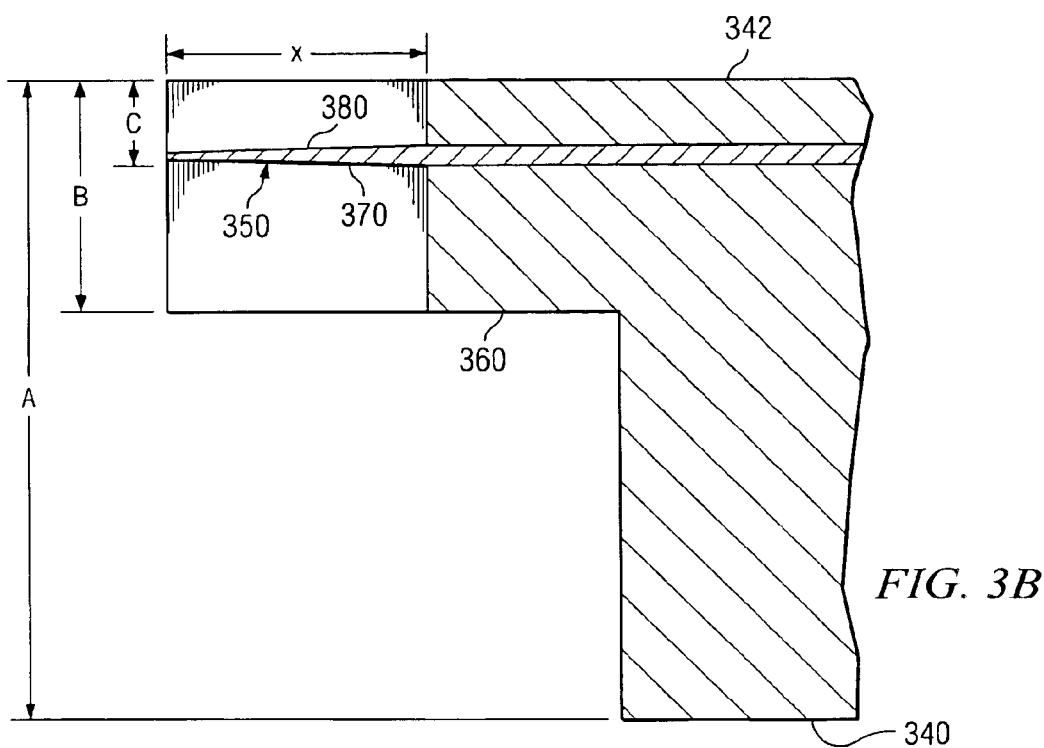

Referring to FIGS. 3A and 3B, sample 300 is a sample prepared according to an embodiment of the present invention. Accordingly, layers 310, 320 and 330 correspond to layers 210, 220 and 230, of sample 200 of FIG. 2B. Additionally, first side 340 is the side opposite of the plan view side of sample 300 and second side 342 is the plan view side 340. First side 340 is created by cutting off a portion of the silicon substrate 330, so that the overall thickness less than the original thickness of the sample 200, and is approximately 100 $\mu$m to 160 $\mu$m. After forming first side 340, a first thinned surface 360 is formed by cutting or mask etching a portion of layer 330 to result in sample 300 having a thickness B which is less than thickness A (e.g., approximately 35 $\mu$m) in the area of sample 300 near the site of interest 350. In the present embodiment, site of interest 350 is within layer 320 of sample 300, but in other embodiments, site 350 may be in another layer or other layers of sample 300.

Second thinned surface 370 is created by two consecutive steps designed to further thin site of interest 350 to a thickness C which is less than thickness B. In the first step, focused ion beam milling is used to thin site of interest 350 at first thinned surface 360 to a roughly uniform thickness of approximately 2 $\mu$m. It is not of uniform thickness due to the well known slope variation generated by FIB milling from the edge of a sample to the thicker portions of a sample. After thinning site of interest 350 to approximately 2 $\mu$m, a silicon-specific etch is performed at site of interest 350 on the first side 340 to further reduce the thickness of the site of interest 350 in a uniform manner. In a particular embodiment, a silicon-specific etch may be used which allows a polysilicon layer or an oxide layer to remain intact while all of the remaining silicon substrate is removed. In a particular embodiment, sample 350 may be ready for TEM analysis after creating side 370 on sample 300. In another embodiment, a third thinned surface 380 is created by a second FIB milling on the first side 342 at site of interest 350. This second FIB milling may be necessary when site of interest 350 is located in a layer of sample 300 that is disposed a distance from second side 342 that is greater than electron transparency.

In one embodiment of the present invention, thickness A, defining the distance from first side 340 to second side 342 may be 160 $\mu$m. Also, in a particular embodiment, thickness B defining the substantially normal distance from first thinned surface 360 to second side 342 may be 35 $\mu$m. In these particular embodiments as well as others, site of interest 350 may have electron transparency for a region having a dimension of up to 50 $\mu$m or more as measured along the x-axis defined on FIGS. 3A and 3B.

Although the present invention has been described in detail, it should be understood that various changes, substitutions, and alterations may be made, without departing from the spirit and scope of the present invention as defined by the claims. For example, the sample material may be gallium arsenide, indium oxide, a suitable metal, metal alloy, or any other solid material that is capable of analysis or imaging through transmission electron microscopy.

What is claimed is:

1. A method of preparing a sample comprising:

preparing a sample so that a site of interest is adjacent a first side of the sample;

removing a first portion of a substrate on the first side of the sample using a first application of a focused ion beam; and removing a second portion of the substrate on the first side by chemical etching comprising chlorine.

2. The method of claim 1, further comprising removing a portion of material from a second side of the sample using a second application of a focused ion beam.

3. The method of claim 1, wherein the chemical etching is performed using a silicon-specific etchant.

4. The method of claim 3, wherein the etching is a wet etch.

5. The method of claim 3, wherein the etching is a plasma etch.

6. The method of claim 1, wherein the chemical etching further comprises:

a second etch, comprising a hydrofluoric acid solution.

7. A method of preparing an analytical sample comprising:

preparing a sample so that a site of interest is adjacent a first side of the sample;

removing a first portion of a substrate on the first side of the sample using a first application of a focused ion beam; and removing a second portion of the substrate on the first side by chemical etching comprising a hydrofluoric acid and nitric acid etch.

8. The method of claim 1, wherein the site of interest is pre-marked using an optical microscope.

9. The method of claim 1, further comprising the step of thinning the sample to a thickness of about 100 $\mu$m to 200 $\mu$m prior to performing the step of removing a first portion of the substrate.

10. The method of claim 9, wherein the sample is thinned by a wafer saw.

11. The method of claim 9, further comprising the step of thinning a strip of the sample along an edge of the site of interest by removing a portion of the sample on a first side of the site of interest.

12. The method of claim 11, wherein the step of thinning a strip of the sample is performed by either sawing or a mask etch.

13. A method of preparing a semiconductor sample comprising:

separating a sample from a semiconductor device such that a site of interest is adjacent a first side of the sample;

performing a first thinning of the sample by removing a first portion of the substrate;

removing substantially all of the substrate in the area near the site of interest by using a focused ion beam; and removing remaining substrate material using a substrate-specific etch comprising a chemical selected from the group consisting of chlorine, hydrofluoric acid and nitric acid etch.

14. The method of claim 13, wherein the first thinning comprises removing a portion of the substrate over the entire surface area of the first side.

15. The method of claim 13, further comprising a second thinning of the sample along a strip of the sample near the site of interest by removing a second portion of the substrate.

16. The method of claim 14, wherein the second thinning creates a stepped configuration adjacent the site of interest.

17. The method of claim 13, further comprising performing a third thinning of the sample on a second side of the sample near the site of interest using a focused ion beam.

18. A semiconductor sample produced in accordance with the process of claim 13.

* * * * *